(12) United States Patent
Kanaoka et al.

(10) Patent No.: US 9,107,977 B2
(45) Date of Patent: Aug. 18, 2015

(54) IMPLANT MATERIAL, IMPLANT COMPONENT, IMPLANT COMPONENT MANUFACTURING METHOD, LASER MACHINING METHOD, AND LASER MACHINING APPARATUS

(75) Inventors: Masaru Kanaoka, Tokyo (JP); Taira Ogita, Tokyo (JP); Shigeru Tadano, Sapporo (JP)

(73) Assignees: Mitsubishi Electric Corporation, Tokyo (JP); National University Corporation Hokkaido University, Sapporo-shi (JP)

( * ) Notice: Subject to any disclaimer, the term of this patent is extended or adjusted under 35 U.S.C. 154(b) by 99 days.

(21) Appl. No.: 13/881,998

(22) PCT Filed: Oct. 27, 2011

(86) PCT No.: PCT/JP2011/074865
§ 371 (c)(1),
(2), (4) Date: Apr. 26, 2013

(87) PCT Pub. No.: WO2012/057287
PCT Pub. Date: May 3, 2012

(65) Prior Publication Data
US 2013/0213553 A1 Aug. 22, 2013

(30) Foreign Application Priority Data
Oct. 29, 2010 (JP) ................................. 2010-244809

(51) Int. Cl.
*A61L 27/10* (2006.01)
*C04B 35/447* (2006.01)
*A61C 8/00* (2006.01)
*A61C 13/00* (2006.01)
*A61L 27/12* (2006.01)

(52) U.S. Cl.
CPC ............... *A61L 27/10* (2013.01); *A61C 8/0012* (2013.01); *A61C 13/0018* (2013.01); *A61L 27/12* (2013.01); *C04B 35/447* (2013.01); *A61L 2430/02* (2013.01)

(58) Field of Classification Search
CPC ........ C04B 35/447; A61L 27/12; A61L 27/10; A61C 8/0012

USPC .......... 501/1, 54, 32; 623/6.11, 23.56; 106/35
See application file for complete search history.

(56) References Cited

U.S. PATENT DOCUMENTS 5,618,762 A * 4/1997 Shirakawa et al. ............... 501/1
2010/0049179 A1 2/2010 Kanaoka et al.

FOREIGN PATENT DOCUMENTS

| CN | 1060282 A | 4/1992 |
| CN | 101505689 A | 8/2009 |
| JP | 64-032867 A | 2/1989 |
| JP | 03-182244 A | 8/1991 |
| WO | 2008/023708 A1 | 2/2008 |

OTHER PUBLICATIONS

Japanese Office Action, dated Jun. 17, 2014, Application No. 2012-540944.
Extended European Search Report, dated Jul. 10, 2014, Application No. 11836420.7.
Chinese Office Action, mailed (First Office Action) Mar. 24, 2014, Application No. 2011800529043.
Taria Ogita et al., "Laser Bonding of Hydroxyapatite Ceramics", Transactions of the Japan Society of Mechanical Engineers, Jun. 21, 2011, pp. 537-544, vol. 77, No. 774.
Communication dated Dec. 12, 2014, issued by the State Intellectual Property Office of P.R. China in counterpart Chinese application No. 201180052904.3.

* cited by examiner

*Primary Examiner* — Karl Group
(74) *Attorney, Agent, or Firm* — Sughrue Mion, PLLC; Richard C. Turner (57) ABSTRACT

In a hydroxyapatite to be joined to another hydroxyapatite or a bone by laser machining (machining of the bone and the hydroxyapatite includes irradiation of laser light on the bone and irradiation of laser light on the hydroxyapatite), to prevent occurrence of a fracture in a junction and in a peripheral portion of the junction during laser machining, the present invention provides an optimum weight ratio of a cordierite or quartz glass component mixed in the hydroxyapatite. As a mixing ratio of the cordierite or quartz glass component, the cordierite or quartz glass component is mixed at least at a weight ratio equal to or higher than 25.7%.

3 Claims, 6 Drawing Sheets

FIG.1

| PENETRATION DEPTH | CORDIERITE (%)/HYDROXYAPATITE (%) | | | | | | | | | | |
|---|---|---|---|---|---|---|---|---|---|---|---|
| | 0%/100% | 10%/90% | 20%/80% | 30%/70% | 40%/60% | 50%/50% | 60%/40% | 70%/30% | 80%/20% | 90%/10% | 100%/0% |
| 1mm | × | × | × | ○ | ○ | ○ | ○ | ○ | ○ | ○ | ○ |
| 3mm | × | × | × | × | ○ | ○ | ○ | ○ | ○ | ○ | ○ |
| 5mm | × | × | × | × | × | × | ○ | ○ | ○ | ○ | ○ |
| 7mm | × | × | × | × | × | × | × | ○ | ○ | ○ | ○ |
| 10mm | × | × | × | × | × | × | × | × | ○ | ○ | ○ |

FIG.2

| PENETRATION DEPTH | LASER OUTPUT | IRRADIATION TIME |
|---|---|---|
| 1mm | 300 TO 500W | 0.4 TO 0.9 SECOND |
| 3mm | 400 TO 600W | 0.5 TO 1.3 SECOND |
| 5mm | 500 TO 700W | 0.6 TO 1.5 SECOND |
| 7mm | 600 TO 800W | 0.7 TO 1.8 SECOND |
| 10mm | 700 TO 900W | 0.9 TO 2.2 SECOND |

FIG.3

| SURFACE PHOTOGRAPHS | | | | |
|---|---|---|---|---|
| CORDIERITE (%)/ HYDROXYAPATITE (%) | 50%/50% | 60%/40% | 70%/30% | 90%/10% |

| | $SiO_2$ | $Al_2O_3$ | MgO | $Na_2O$ | CaO | Expansion coefficient ($\times 10^{-7}$°$C^{-1}$·cm) |
|---|---|---|---|---|---|---|
| Silica glass | 100 | - | - | - | - | 5.9 TO 6.9 |
| Cordierite | 53.9 | 32.2 | 13.9 | - | - | 20 TO 25 |
| Soda glass | 71.9 | - | - | 13.3 | 7.8 | 99 |

IMPLANT MATERIAL, IMPLANT COMPONENT, IMPLANT COMPONENT MANUFACTURING METHOD, LASER MACHINING METHOD, AND LASER MACHINING APPARATUS

CROSS REFERENCE TO RELATED APPLICATIONS

This application is a National Stage of International Application No. PCT/JP2011/074865 filed Oct. 27, 2011, claiming priority based on Japanese Patent Application No. 2010-244809 filed Oct. 29, 2010, the contents of all of which are incorporated herein by reference in their entirety.

FIELD

The present invention relates to a material for combining ceramic hydroxyapatites, which are biomaterials, or combining a hydroxyapatite and a natural bone, a component made of the material, a method of manufacturing the component, a machining method, and a machining apparatus.

BACKGROUND

In joining of biological tissue substitute components made of ceramic hydroxyapatites, which are biomaterials, machining has been difficult because a fracture (also referred to as crack) occurs in the hydroxyapatites in a melting process for the hydroxyapatites. Therefore, as a method of forming the hydroxyapatites in a component shape, molding by a die or machining has been generally adopted.

It is known that, in a machining method for combining a bone tissue and an implant material such as ceramic, which is a biomaterial, or a composite material, a texture machined surface is used for the implant material to enhance bone adhesion and, therefore, to stabilize the position of the implant material (a surgical transplant material) with respect to a bone. For example, in an artificial hip including a thighbone sub-aggregate fixedly attached in the thighbone of a patient and an acetabulum sub-aggregate fixedly placed in the acetabulum of the patient, the thighbone sub-aggregate representatively includes an artificial stem provided with a texture machined surface and the acetabulum sub-aggregate representatively includes an artificial cup provided with the texture machined surface. The texture machined surfaces are provided to facilitate proliferation of bones. However, texture machined surfaces are positioned until adhesion and fixed by plaster casts after setting. A period of several months is sometimes required until fixation.

Therefore, to realize a reduction and stabilization of a time for joining the implant material and the bone tissue, a technology for joining the implant material and the bone tissue using laser machining has been disclosed (see, for example, Patent Literature 1). A technology for realizing improvement of biocompatibility and high toughness of adhesion to a tissue has also been disclosed (see, for example, Patent Literature 2).

CITATION LIST

Patent Literature

Patent Literature 1: WO 2008/023708
Patent Literature 2: Japanese Patent Application Laid-Open No. S64-032867

SUMMARY

Technical Problem

In general machining of a component made of a hydroxyapatite, a method of molding by a die or forming by machining has been adopted. Therefore, there is a problem in that a machining time and machining costs increase. In particular, in manufacturing of a component having a complicated shape in a portion and having a simple shape in the other portion, it is desirable to adopt a manufacturing process for separately manufacturing the complicated portion and the simple portion and joining the respective portions in a post-process. However, because there is the problem of a crack as explained above, the manufacturing cannot be realized. It has been necessary to integrally form the portions. As a result, a long machining time and high machining costs have been required.

If laser welding can be adopted for these kinds of machining of a component made of a hydroxyapatite, a significant effect may be exerted for a reduction in the machining time and the machining costs.

In the method of laser-joining the implant material and the bone tissue described in Patent Literature 1, a ratio of a cordierite component contained in a hydroxyapatite, which is an implant material, is not specified. Therefore, joining has been defective in some cases. As a main joining defect, a fracture occurs in a junction of the hydroxyapatite or in the vicinity of the junction. Therefore, a reduction of the joining defect is necessary in the joining of the hydroxyapatite and the bone tissue.

In the technology described in Patent Literature 2, a cordierite component $SiO_2+Al_2O_3+MgO$ and a quartz glass component $SiO_2$ are specified. However, combinations of the cordierite component and the quartz glass component with the hydroxyapatite are not specified. This is because laser machinability and effectiveness of joining with the hydroxyapatite are not taken into account.

Solution to Problem

To solve the problems explained above and achieve an object, the inventor earnestly conducted researches and found out that a weight ratio of the cordierite component mixed in the hydroxyapatite is closely related to a fracture in the junction and in the vicinity of the junction in the laser machining. In a hydroxyapatite to be joined to another hydroxyapatite or a bone by laser machining (machining of the bone and the hydroxyapatite includes irradiation of the bone with laser light and irradiation of the hydroxyapatite with laser light), to prevent occurrence of a fracture in a junction and in a peripheral portion of the junction during laser machining, the present invention provides an optimum weight ratio of a cordierite or quartz glass component mixed in the hydroxyapatite. As a mixing ratio of the cordierite or quartz glass component, the cordierite or quartz glass component is mixed at least at a weight ratio equal to or higher than 25.7%.

The present invention provides a laser machining apparatus including: a laser irradiating unit configured to irradiate, with laser light, a joining position of the hydroxyapatites in which the cordierite or quartz glass component is mixed at least at the weight ratio equal to or higher than 25.7% or a joining position of a bone and the hydroxyapatite in which the cordierite or quartz glass component is mixed at least at the weight ratio equal to or higher than 25.7%; a machining-condition determining unit configured to determine a machining condition in joining the hydroxyapatites or the bone and the hydroxyapatite; and a control unit configured to control, based on the machining condition determined by the machining-condition determining unit, the irradiation in joining the bone and the hydroxyapatite with the laser light.

Further, the present invention provides an implant component manufacturing method for joining, by irradiating with the laser light, the hydroxyapatites in which the cordierite or quartz glass component is mixed at least at the weight ratio equal to or higher than 25.7% or a bone and the hydroxyapatite in which the cordierite or quartz glass component is mixed at least at the weight ratio equal to or higher than 25.7% to manufacture an implant component having a new shape.

Advantageous Effects of Invention

According to the present invention, because the cordierite or quartz glass component is mixed in the hydroxyapatite at least at the weight ratio equal to or higher than 25.7%, it is possible to prevent a fracture from occurring in a junction of the hydroxyapatite or vicinity of the junction when the hydroxyapatites themselves are joined or the bone or the hydroxyapatite are joined by irradiating them with laser light. Consequently, there is an effect that it is possible to easily join the hydroxyapatites or join the bone and the hydroxyapatite in a short time using the laser machining.

DESCRIPTION OF EMBODIMENTS

First Embodiment

Figure 1:
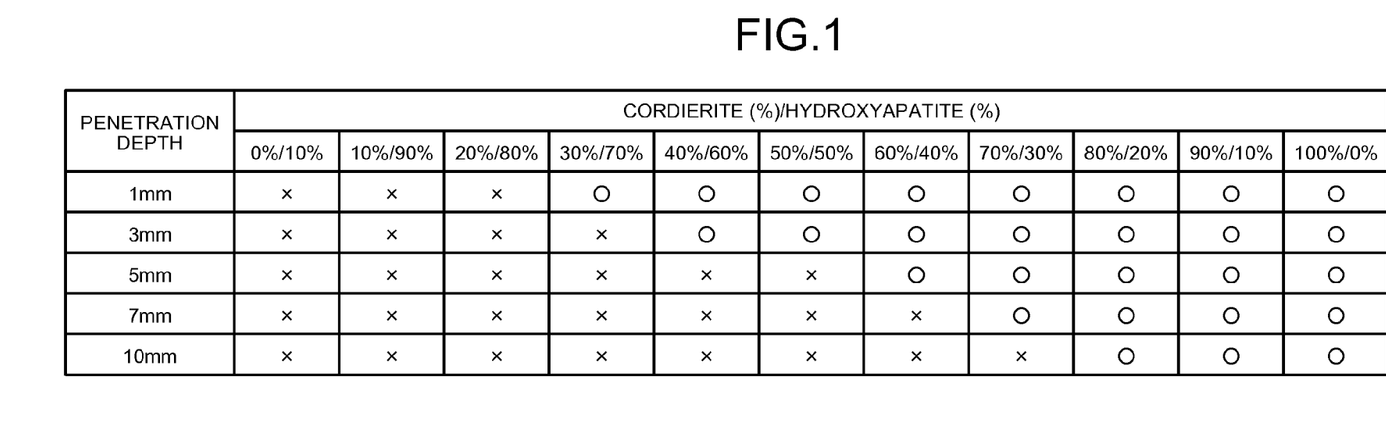
FIG. 1 is a diagram of a relation between a mixing ratio and occurrence of a fracture that occurs when an implant material in which a cordierite is mixed in a hydroxyapatite is irradiated with laser light.

FIG. 1 is a diagram of a result obtained by irradiating an implant component with laser light and checking presence or absence of a fracture (also referred to as a crack). The implant component is manufactured by baking an implant material while changing a mixing ratio of a cordierite, which is a glass biological material, in a hydroxyapatite, which is an implant material, in the implant material. The hydroxyapatite is a substance indicated by a chemical formula "$Ca_{10}(PO_4)_6(OH)_2$". The cordierite is a substance formed of silicon oxide ($SiO_2$), which is a glass component having a small coefficient of thermal expansion, aluminum oxide ($Al_2O_3$), or magnesium oxide (MgO). The implant component was manufactured by changing, as a mixing ratio of the hydroxyapatite and the cordierite, a weight ratio (cordierite (%)/hydroxyapatite (%)) at an interval of 10% from 0% to 100% and 100% to 0%, respectively.

Figure 2:
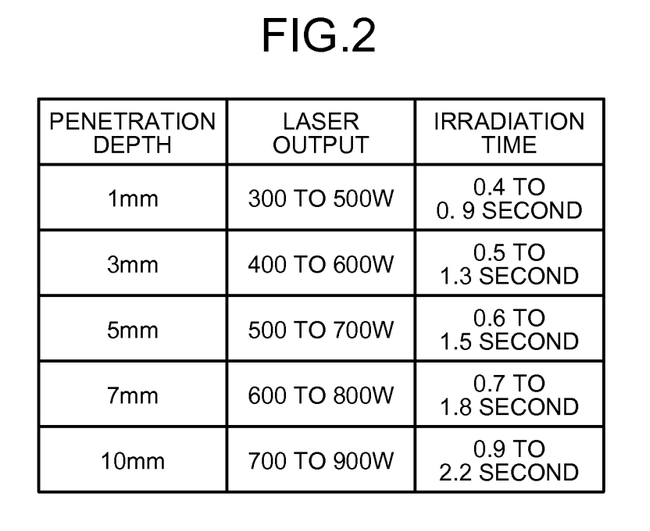
FIG. 2 is a diagram of laser machining conditions for obtaining a table shown in FIG. 1.

Concerning laser machining conditions, penetration depth of the implant material to the implant component in a section to be irradiated with laser light was set to be five kinds including 1 mm, 3 mm, 5 mm, 7 mm, and 10 mm. The penetration depth is a distance from a melted lowest position from the surface on a side of the implant component irradiated with the laser light. Specific machining conditions are shown in FIG. 2. In FIG. 2, a range of a laser output, for example, a laser output of 300 to 500 W in the case of a penetration amount of 1 mm is a range in which proper penetration depth is obtained and foaming necessary in joining explained below is obtained. An irradiation time is time from the start of the laser irradiation until completion of the foaming. In this experiment, the irradiation time tended to be shorter as the laser output was larger. Other machining condition parameters not shown in the figure are duty: 10%, a laser type: $CO_2$, a lens focal distance: 7.5 inches, an assist gas type: Ar, an assist gas flow rate: 10 liters/minute, and a nozzle diameter: 2 mm. However, the other machining condition parameters are not predominant concerning an ability of joining, which is the object of the present invention. The other machining condition parameters are parameters for controlling the quality of a junction. Numerical values described in the figure are not essential and need to be corrected according to a situation.

In FIG. 1, machining in which a fracture occurred is indicated by an x-mark and machining in which a fracture did not occur is indicated by a white circle. In laser machining with small penetration depth of 1 mm, a fracture did not occur in a range in which a cordierite amount was increased from a ratio 30%/70% of cordierite (%)/hydroxyapatite (%). As the penetration depth increased, a boundary between a region where a fracture occurred and a region where a fracture did not occur shifted to a region where the cordierite amount was increased. In a condition the laser output was equal to or smaller than 1 kW, a relation between occurrence of a fracture and a mixing ratio of the cordierite was the same as FIG. 1 at all penetration amounts including a penetration amount with which appropriate foaming was not obtained.

Figure 3:
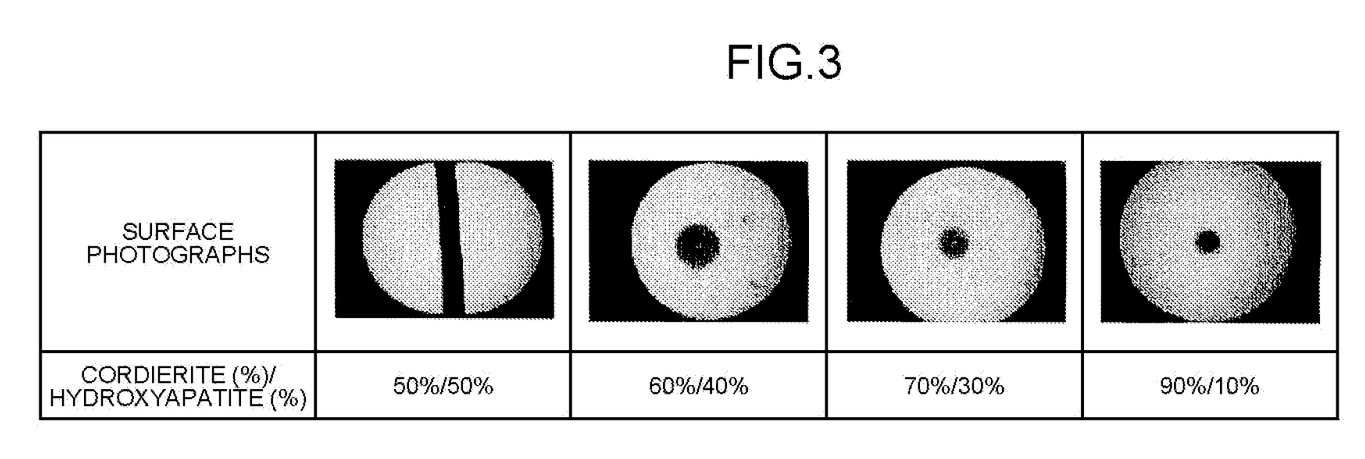
FIG. 3 is surface photographs of an implant component which is irradiated with laser light.

FIG. 3 is actual surface photographs of an implant component that is irradiated with laser light to obtain the result of FIG. 1. As experiment conditions, the implant component was irradiated with the laser light at a laser output of 600 W and an irradiation time of 0.9 second to obtain penetration depth of 5 mm. As it is seen from FIG. 3, at a ratio 50%/50% of cordierite (%)/hydroxyapatite (%), a workpiece is fractured to the left and right. At ratios 60%/40%, 70%/30%, and 90%/10% of cordierite (%)/hydroxyapatite (%), no fracture occurs and melted traces are seen around an irradiation position with the laser light.

Figure 4:
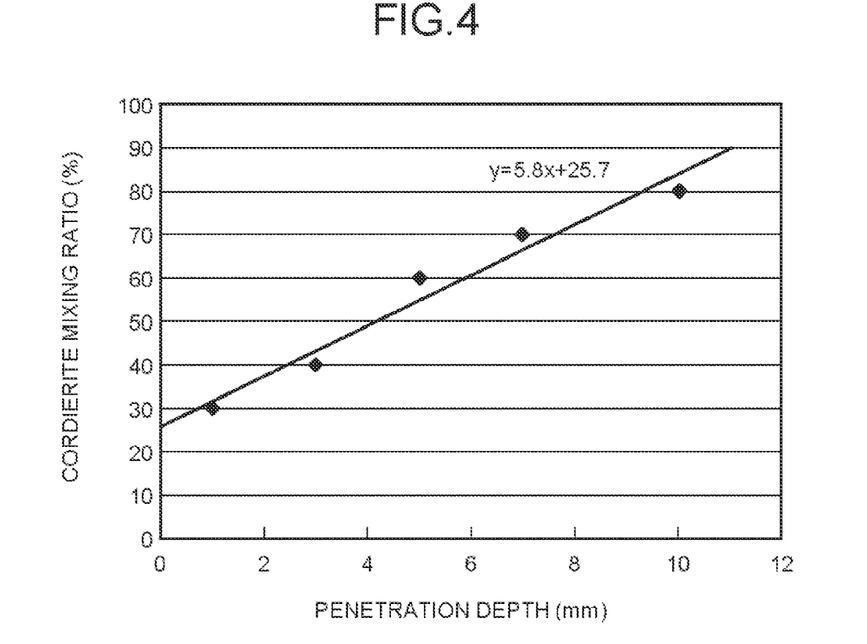
FIG. 4 is a graph of a relation between a mixing ratio and occurrence of a fracture in the case the implant material in which the cordierite is mixed in the hydroxyapatite is irradiated with the laser light.

As shown in FIGS. 1 and 3, it was found that a fracture is not caused by being irradiated with laser in an implant component manufactured from an implant material in which the cordierite is mixed in the hydroxyapatite at an appropriate weight mixing ratio. As shown in FIG. 1, because a fracture occurs at all penetration depths if the cordierite weight mixing ratio is smaller than 30%, the cordierite weight mixing ratio at least equal to or larger than 30% is necessary to obtain penetration depth of 1 mm. It was found that it is necessary to increase the weight mixing ratio of the cordierite when penetration depth is further increased to realize improvement of joining strength. The increase in the weight mixing ratio is clarified by representing, as a graph, the penetration depth of the laser irradiation section in FIG. 1 and a minimum weight mixing ratio of the cordierite at which no fracture occurred at respective penetration depths. FIG. 4 is the graph. A mixing ratio of the cordierite at which a fracture does not occur can be represented by the following formula according to FIG. 4:

$$W(\%) \geq 5.8 \times \times D(\text{mm}) + 25.7 \quad \text{(Formula 1)}$$

where, W (%) indicates the weight mixing ratio of the cordierite and D (mm) indicates the penetration depth of the section that is irradiated with laser. When D is set to 0, because W is 25.7, the minimum weight ratio can be set to 25.7%. (Formula 1) is obtained by directly converting the result shown in FIG. 1 into a graph and subjected to linear approximation. However, actually, it is likely that an error of about 20% occurs in the mixing ratio of the cordierite. This is because, porosities are respectively determined for ceramics such as the hydroxyapatite and an error of about 20% is likely to occur according to a difference of the porosities. A maximum value of the mixing ratio is 100%. Essential machining conditions are the output and the irradiation time shown in FIG. 2. When the output is too low, a thermal effect is increased. When the output is too high, a fracture due to a thermal shock easily occurs. Therefore, preferential setting is necessary for the output. After the output is determined, the irradiation time is set such that predetermined penetration depth is obtained according to the output. Therefore, a parameter of the irradiation time is ranked subordinate. The other condition parameters are as explained with reference to FIG. 1.

As explained above, when the penetration depth of the laser irradiation section increases, the mixing ratio of the cordierite needs to be increased. A reason for the increase in the mixing ratio is presumed as explained below. That is, a crack due to the laser irradiation is caused by suppression of thermal expansion. As a penetration amount increases, a crack more easily occurs because force of the suppression increases. Because of the same reason, in cutting of ceramics or quartz glass, a thin plate can be cut without a crack but, when plate thickness increases, the ceramics or the quartz glass is fractured. Meanwhile, it is possible to increase a component having a small expansion coefficient by increasing the mixing ratio of the cordierite. Consequently, an amount of thermal expansion decreases and a crack less easily occurs. This is a reason for the results shown in FIGS. 1 and 3.

Figure 5:
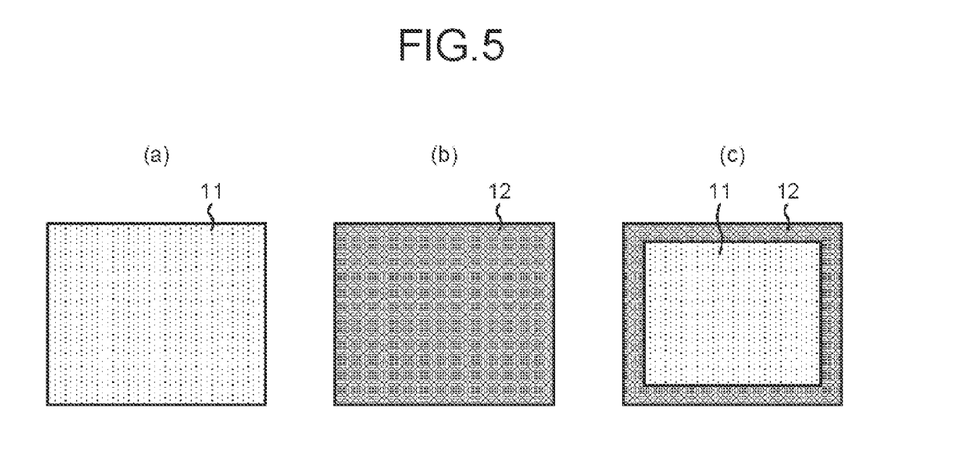
FIG. 5 is a sectional view of an implant component made of an implant material according to the present invention.

In the experiment in FIG. 1, the entire implant component is molded from the implant material manufactured at a predetermined cordierite mixing ratio irrespective of the penetration depth of the implant material of the laser irradiation section. However, actually, it is unnecessary to manufacture the entire implant component from the implant material having the predetermined cordierite mixing ratio. A mixing ratio in only a portion to be melted during laser machining has to satisfy (Formula 1). FIG. 5 is a schematic diagram of a cross section of an implant component in which the hydroxyapatite and the cordierite are mixed. FIG. 5(a) is a diagram of a cross section of a general implant component of a hydroxyapatite 11 that has existed from the past. FIG. 5(b) is a diagram of a cross section of an implant component molded from an implant material 12 in which the cordierite is uniformly mixed in the hydroxyapatite in the present invention. FIG. 5(c) is a diagram of a cross section of an implant component including the implant material 12 in which the cordierite is uniformly mixed to predetermined depth in a surface portion of the implant component of the hydroxyapatite 11 in the present invention.

In joining of the implant component by the laser light, a surface layer of the implant component is melted and combined. Therefore, as shown in FIG. 5(c), only the surface layer to be melted by irradiation with the laser light may be a constituent tissue suitable for joining in which the hydroxyapatite and the cordierite are mixed. In this case, a mixing ratio of the cordierite only has to be determined from (Formula 1) using the thickness of the surface layer as the penetration depth. On the other hand, as shown in FIG. 5(b), the entire implant component is the constituent tissue in which the hydroxyapatite and the cordierite are mixed. In this case, when the implant component is divided and joined by the laser light, even if the laser joining surface is an inside that appears according to the division of the implant component, it is possible to take measures to make the mixing ratio of the cordierite appropriate and prevent a fracture from occurring.

In the above explanation, the cordierite, which is the glass biomaterial, is mixed in the hydroxyapatite, which is the implant material. However, it was found that the same effect is obtained when quartz glass, which is also a glass biomaterial, is mixed in the hydroxyapatite instead of the cordierite. Concerning a relation between occurrence of a fracture of the implant component and a weight mixing ratio of the quartz glass, a result same as the result shown in FIGS. 1 and 4 was obtained. Further, when a mixture of the cordierite and the quartz glass is mixed in the hydroxyapatite, concerning a weight ratio of the mixture of the cordierite and the quarts glass and the hydroxyapatite and a fracture of an implant material formed by the mixture due to irradiation with laser, an effect same as the effect in FIGS. 1 and 4 was obtained.

Figure 6:
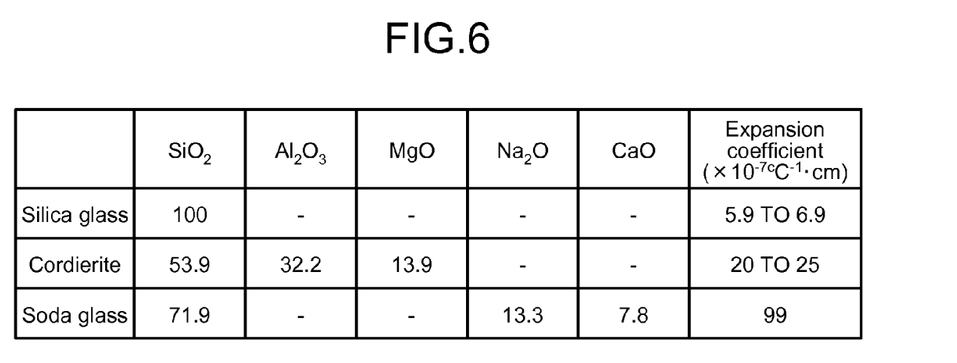
FIG. 6 is a table of components and coefficients of thermal expansion of various materials mixed in the hydroxyapatite.

In general, in melting by local heating of ceramic, a crack is caused by expansion and contraction of a workpiece. Therefore, the entire workpiece is heated in a furnace and melted and jointed. However, in melting by local heating of an implant component having a mixing ratio 60%/40% of the cordierite and the hydroxyapatite, the coefficient of thermal expansion of the cordierite effectively acts and a crack does not occur. FIG. 6 is a table of components and coefficients of thermal expansion of soda glass, which is representative glass, quartz glass (Silica glass), and cordierite. The quartz glass also shows a sufficiently low coefficient of thermal expansion. As explained above, a crack does not occur as in the cordierite. This indicates that, if a glass biomaterial that can be mixed in the hydroxyapatite has a coefficient of thermal expansion lower than that of the cordierite, the quartz glass is a target that can be joined by laser.

Second Embodiment

Figure 7:
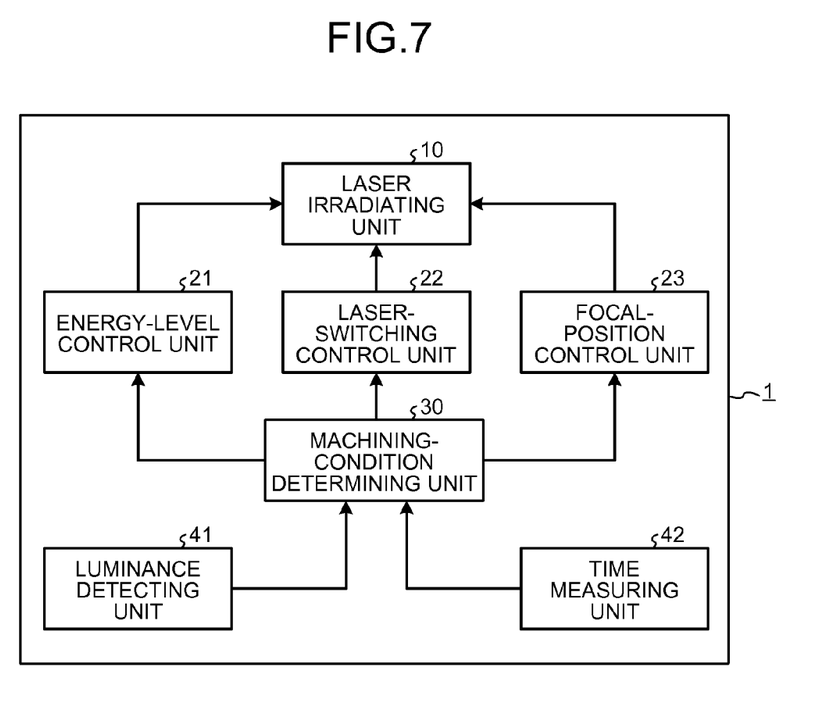
FIG. 7 is a block diagram for explaining the configuration of a laser machining apparatus according to the present invention.

A method and an apparatus for laser-machining the implant component formed of the implant material in which the cordierite or the quartz glass is mixed in the hydroxyapatite at the appropriate weight ratio explained in the first embodiment is explained. FIG. 7 is a block diagram of the configuration of a laser machining apparatus according to an embodiment of the present invention. A laser machining apparatus 1 includes: a laser irradiating unit 10; an energy-level control unit 21; a laser-switching control unit 22; a focal-position control unit 23; a machining-condition determining unit 30; a luminance detecting unit 41; and a time measuring unit 42.

The energy-level control unit 21, the laser-switching control unit 22, and the focal-position control unit 23 are sometimes referred to as control unit as well. The luminance detecting unit 41 and the time measuring unit 42 are sometimes referred to as machining-state detecting unit as well. Luminance detection can be processed as well by visual determination of a skilled operator according to the level of skill of the operator. Therefore, an apparatus not including the luminance detecting unit 41 can also deal with the luminance detection.

The laser machining apparatus 1 uses the implant component obtained by baking the implant material in which the cordierite is mixed in the hydroxyapatite at an appropriate weight ratio explained in the first embodiment and joins a plurality of the implant components themselves or the implant component (an artificial bone or an artificial tooth root) and a bone (or a tooth) using laser machining. The laser machining apparatus 1 is an apparatus that, in a joining process for the implant components or the implant component and the bone or the tooth, irradiates the implant component and the bone with laser based on predetermined control to firmly keep a joining position relation between the implant component and the bone until proliferation of the bone is sufficiently facilitated and in future. The laser machining apparatus 1 irradiates the the implant component and the bone with laser to perforate the implant component and the bone and join the implant component and the bone.

The laser irradiating unit 10 irradiates a workpiece such as the implant component or the bone with the laser. The laser irradiating unit 10 is connected to the energy-level control unit 21, the laser-switching control unit 22, and the focal-position control unit 23. The laser irradiating unit 10 irradiates, based on control by the energy-level control unit 21, the laser-switching control unit 22, and the focal-position control unit 23, the implant component and the bone with laser under predetermined machining conditions.

The laser-switching control unit 22 causes, based on an instruction from the machining-condition determining unit 30, the laser irradiating unit 10 to switch a type of laser light that irradiates the workpiece with the laser irradiating unit 10. The laser-switching control unit 22 selects at least one laser light out of, for example, $CO_2$ laser YAG (Yttrium Aluminum Garnet) laser, CO laser, UV (Ultra Violet rays)-YAG laser, fiber laser, green laser, and excimer laser and causes the laser irradiating unit 10 to switch the type of the laser light that irradiates the workpiece with the laser irradiating unit 10.

The focal-position control unit 23 controls, based on an instruction from the machining-condition determining unit 30, a focal position of the laser light that irradiates the workpiece with the laser irradiating unit 10 (concentrates the laser light). The energy-level control unit 21 controls, based on an instruction from the machining-condition determining unit 30, an energy level of the laser light that irradiates the workpiece with the laser irradiating unit 10.

The machining-condition determining unit 30 sends instructions to the energy-level control unit 21, the laser-switching control unit 22, and the focal-position control unit 23 to irradiate the implant component and the bone with laser under the predetermined machining conditions. The machining-condition determining unit 30 sends an instruction concerning the energy level of the laser light that irradiates the workpiece to the energy-level control unit 21, sends an instruction concerning the type of the laser light that irradiates the workpiece to the laser-switching control unit 22, and sends an instruction concerning the focal position of the laser light that irradiates the workpiece to the focal-position control unit 23.

The machining-condition determining unit 30 determines, based on the luminance of the workpiece received from the luminance detecting unit 41 and a measured time (e.g., time from the start of laser machining) received from the time measuring unit 42, machining conditions in irradiating the implant component and the bone with laser. The machining-condition determining unit 30 then sends the instructions to the energy-level control unit 21, the laser-switching control unit 22, and the focal-position control unit 23 based on the determined machining conditions.

The luminance detecting unit 41 detects the luminance of the workpiece (the luminance of a laser light at the section of the workpiece that is irradiated) as a machining state of the workpiece and sends the luminance of the workpiece to the machining-condition determining unit 30. The time measuring unit 42 measures, as a machining state of the workpiece, for example, an elapsed time from the start of the laser machining, an elapsed time from the start of the perforation of the implant component, an elapsed time from the start of the perforation of the bone, and an elapsed time of irradiation, with the laser light, of a junction (a combined portion of the bone and the implant component) to join the implant component and the bone and sends the elapsed time being measured to the machining-condition determining unit 30.

Specific laser machining by the laser machining apparatus 1 is explained. The laser irradiating unit 10 of the laser machining apparatus 1 applies, for example, as the laser light, light having high energy density equal to or higher than $10^3$ W/cm$^2$ condensed in a diameter equal to or smaller than about 0.3 mm. Consequently, it is possible to narrow down a machining region by the laser light and locally heat the machining region and apply perforation and melting to the workpiece in a short time. The laser machining apparatus 1 can control time for melting the workpiece, i.e., an irradiation time with the laser light and a melting range of the workpiece according to selection (determination) of a machining condition, i.e., an output condition of the laser light by the machining-condition determining unit 30. The irradiation time with the laser light mainly contributes in the depth direction of the melting range and a condensing diameter of the laser light mainly contributes in the radial direction of the melting range. The laser machining apparatus 1 can be applied to a wide variety of workpieces such as metal, resin, and ceramics to the perforation and the melting according to the selection of a machining condition by the machining-condition determining unit 30.

Figure 8:
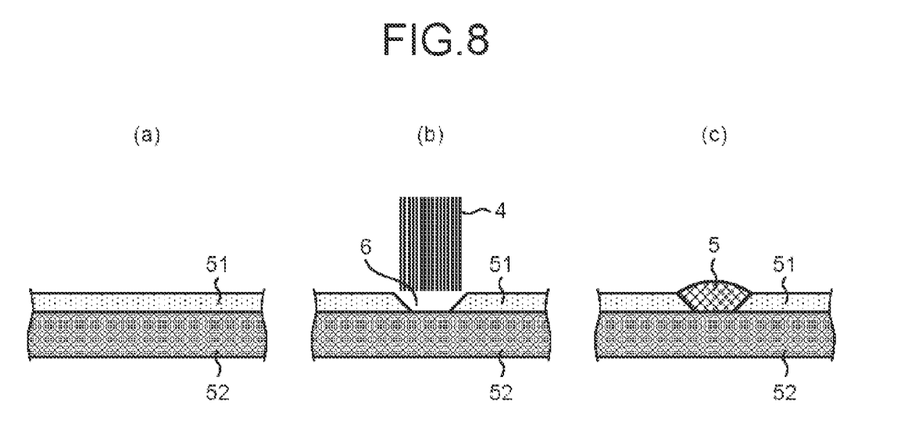
FIG. 8 is a diagram for explaining a process of joining of a bone and the implant component according to the present invention.

A process for performing the perforation of the workpiece as specific laser machining by the laser machining apparatus 1 and thereafter joining the bone and the implant component is explained. FIG. 8 is a diagram for explaining a process in which a bone 51 is irradiated with laser light 4 to carry out perforation and thereafter an implant component 52 arranged under the bone foams and the bone 51 and the implant component 52 are joined. That is, the laser machining is performed with the bone 51 arranged on side to be irradiated with the laser light 4 and the implant component 52 arranged on a counter-irradiation side on the opposite side of the irradiation side with respect to the bone 51. In the following explanation, the irradiation side is simply referred to as upper side or above as well and the counter-irradiation side is simply referred to as lower side or under as well.

Specifically, FIG. 8(*a*) is a diagram in which the implant component 52 having thickness of 5 mm and a mixing ratio 60%/40% of the cordierite and the hydroxyapatite is arranged under the bone 51 having thickness of 1 mm.

FIG. 8(*b*) is a diagram in which the bone 51 and the implant component 52 arranged in the upper and lower sides in FIG. 8(*a*) are irradiated with $CO_2$ laser light 4 from above the bone 51 and perforation is carried out in the bone 51. A hole dimension of the perforation in the bone 51 can be arbitrarily changed by adjusting a focal position where the laser light 4 is condensed. As the perforation by the laser light develops from the surface side to the inside of the workpiece, laser energy is consumed by perforation and attenuates. Therefore, a hole diameter decreases toward the inside. Even when the perforation is performed using the YAG laser having wavelength of 1.06 μm, which is one tenths of the wavelength of the $CO_2$ laser, perforation with a small thermal effect can be performed in the same manner as the $CO_2$ laser.

In the perforation, when the UV-YAG laser or the excimer laser having the wavelength of laser light in an ultraviolet region or the green laser having the wavelength of laser light in a visible light region is used, electron-excited composition and decomposition by ultraviolet light or visible light occurs and photochemical machining (ablation machining) is performed. Therefore, it is possible to reduce a thermal effect on the bone, the implant material, and the like to be smaller than the thermal effects of the $CO_2$ laser, the YAG laser, and the fiber laser, which are infrared lasers.

When the perforation is carried out in the bone and the implant material using the UV-YAG laser, the excimer laser, or the green laser, the perforation finer than the perforation by the $CO_2$ laser and the YAG laser, which are the infrared lasers, is possible. That is, the perforation in the bone and the implant material with a little thermal effect is possible irrespective of a type of a laser in use (the $CO_2$ laser or the YAG laser, which are the infrared lasers, and the UV-YAG laser, the excimer laser, and the green laser, which are the ultraviolet lasers).

The perforation can be performed by all laser lights such as the $CO_2$ laser, the YAG laser, the fiber laser, the excimer laser, and the UV-YAG laser.

In FIG. 8(c), when from a portion perforated in the bone 51 is further irradiated with the $CO_2$ laser light 4, and the implant component 52 is melted, a foaming portion 5 is further generated. Because the hole perforated in the bone 51 is tapered as explained above, when viewed from the implant component 52, the hole is a reversely-tapered hole. Therefore, when the foaming portion 5 enters the hole, as it is evident from FIG. 8(c), the foaming portion 5 less easily escapes in the direction of the implant component 52. Further, because the foaming portion 5 and the implant component 52 are integrated, the implant component 52 is firmly connected to the bone 51. Again, the melting and the foaming of the implant material can be performed by all laser lights such as the $CO_2$ laser, the YAG laser, the fiber laser, the excimer laser, and the UV-YAG laser.

Figure 9:
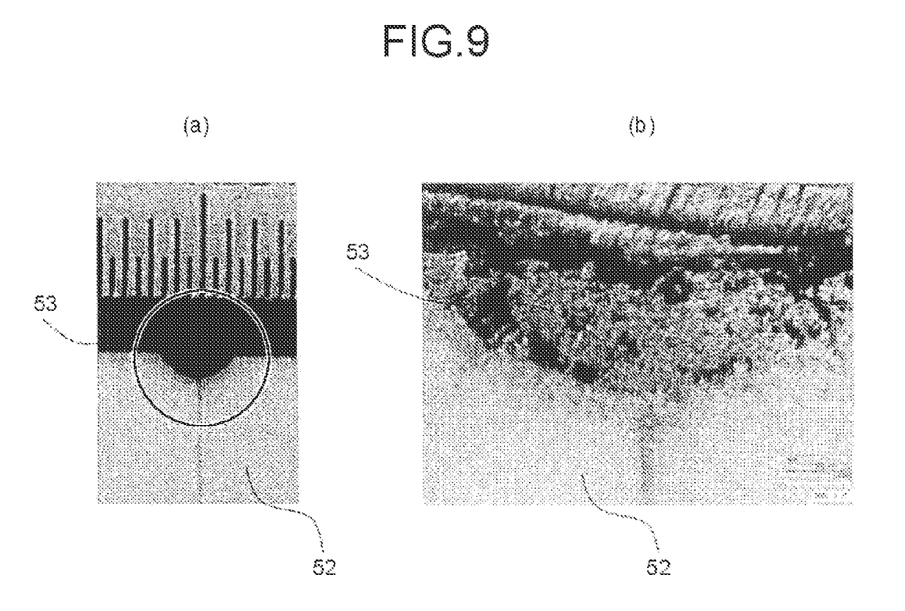
FIG. 9 is photographs of a state of joining of implant components according to the present invention.

FIG. 9 is photographs of a weld bead 53 formed when the workpiece of the implant component 52 having the mixing ratio 60%/40% of the cordierite and the hydroxyapatite was brought into contact with the bone 51 and laser-welded. FIG. 9(a) is a photograph of a contact section and FIG. 9(b) is an enlarged photograph of an encircled portion in FIG. 9(a), i.e., the contact section. The laser welding was carried out under laser machining conditions: the $CO_2$ laser, an output of 400 W, and machining speed of 1 m/min. The width of the weld bead 53 was 2.65 mm and the depth of the weld bead 53 was 1.01 mm. No fracture occurred in a welded section and satisfactory welding quality was obtained.

As the time of the laser irradiation is set longer, a melting region, in particular, a region in the depth direction is expanded. Therefore, the time of the laser irradiation is changed according to the intensity of joining. That is, the machining-condition determining unit 30 sets the laser irradiation time long when high intensity is requested for the joining and sets the laser irradiation time short when high intensity is unnecessary for the joining. The machining-condition determining unit 30 may set the laser irradiation time based on an instruction from a user (a command from an input unit) or may set the laser irradiation time based on luminance detected by the luminance detecting unit 41.

The laser machining apparatus 1 can expand the melting region as well according to adjustment of a focal position or selection of condensing optical component. Therefore, the machining-condition determining unit 30 selects a focal position corresponding to the melting region as a machining condition and instructs the focal-position control unit 23 to adjust the focal position. The laser machining apparatus 1 may be configured to be capable of selecting, for each laser machining, a condensing optical component corresponding to the melting region. For example, the laser machining apparatus 1 is configured to select a condensing optical component having a large focal length when a laser irradiation portion is far from the laser irradiating unit 10 and select a condensing optical component having a small focal length when the laser irradiation portion is close to the laser irradiating unit 10. The laser machining apparatus 1 may be configured to automatically change the condensing optical component based on an instruction from the machining-condition determining unit 30. Naturally, the user of the laser machining apparatus 1 may manually change the condensing optical component in advance.

The laser machining apparatus 1 may use any laser oscillator and any condensing optical component. For example, in the perforation process, the laser machining apparatus 1 can obtain a very small hole by using a laser oscillator and a condensing optical component that can obtain high energy density.

With the implant material having the mixing ratio in the first embodiment, a satisfactory junction is obtained under normal laser machining conditions. However, under abnormal laser machining conditions, for example, at an excessive laser output or irradiation time, unsatisfactory joining may be performed in some case. The luminance in the vicinity of the junction is different when the satisfactory junction is obtained and when unsatisfactory joining is performed. Therefore, for example, when the laser machining apparatus 1 performs the laser machining without performing monitoring of luminance, if there is a problem in setting of the laser machining conditions, laser energy equal to or larger than a heat input necessary for the perforation and the joining is applied to the bone 51 and the implant component 52 in some case. When there is an excessive heat input, a portion affected by a thermal effect in the workpiece increases and a melted material does not coagulate and scatters. Therefore, joining is not satisfactorily performed. On the other hand, in the laser machining apparatus 1 according to the second embodiment, the luminance detecting unit 41 performs detection (monitoring) and machining conditions are determined using the detected luminance. Therefore, even if the machining conditions are abnormal, it is possible to obtain a satisfactory junction.

In the explanation in the second embodiment, the laser machining apparatus 1 includes the luminance detecting unit 41 and the time measuring unit 42. However, the laser machining apparatus 1 may not include the luminance detecting unit 41 and the time measuring unit 42. In this case, the user of the laser machining apparatus 1 detects a machining state of the workpiece through a visual observation and the machining-condition determining unit 30 determines machining conditions based on an input of instruction information from the user. That is, the laser machining apparatus 1 determines machining conditions for the workpiece without performing detection of a machining state by the luminance detecting unit 41 and the time measuring unit 42. Naturally, if appropriate machining conditions are set, with the implant material having the mixing ratio in the first embodiment, it is possible to obtain satisfactory joining without worrying about luminance.

The machining-condition determining unit 30 determines machining conditions based on the luminance detected by the luminance detecting unit 41 and the time measured by the time measuring unit 42 and applies the laser irradiation to the workpiece. Therefore, it is possible to perform appropriate laser irradiation and joining corresponding to the workpiece. Among the treatments of the laser machining apparatus 1 explained in the second embodiment, all or a part of the treatments explained as being automatically performed can be manually performed.

The machining-condition determining unit 30 determines, as machining conditions, an energy level of laser light, a type of the laser light, a focal position, an irradiation time of the laser light, and the like and applies laser irradiation to the workpiece based on the determined machining conditions. Therefore, it is possible to perform stable appropriate perforation and joining for each perforation and joining of the workpiece.

Third Embodiment

The implant component molded from the implant material in which the cordierite is mixed in the hydroxyapatite at the appropriate weight ratio explained in the first embodiment is joined by the laser light using the laser machining apparatus and the laser machining method explained in the second embodiment. This makes applications explained below possible.

Laser machining according to the present invention makes melting of ceramic that does not adversely affect a living organism in a narrow space in a surgical operation and does not cause a crack possible. That is, with the implant material according to the first embodiment, a crack does not occur under normal machining conditions. The heating by the laser light from the laser machining apparatus 1 (the laser irradiating unit 10) has a characteristic that, according to an instruction of machining conditions by the machining-condition determining unit 30 (control from the energy-level control unit 21, the laser-switching control unit 22, and the focal-position control unit 23), machining is finished in a range in which a region for heating workpiece is spatially and temporally limited. The heating is effective as a surgical operation method as well.

The laser machining apparatus 1 can complete machining in a short time by using a laser oscillator and a condensing optical component having high energy density. Therefore, it is possible to reduce a thermal effect on the bone 51 and the implant component 52.

In the workpiece machined by the laser machining apparatus 1, whichever of the bone 51 and the implant component 52 can be arranged above and can be arranged below. A joint for the bone 51 and the implant component 52 may be either a lap splice or a butt joint. The bone in the present invention may be obtained by laser-machining a bone of an animal including a human bone.

In the present invention, the bone and the implant component can be easily joined in a short time. Therefore, in treatment for joining the bone and the implant component, it is possible to prevent a shift from occurring in a positional relation between the implant component and the bone during joining of the implant component and the bone and it is possible to easily perform the treatment in a short period. A large-scale jig for fixing necessary during joining treatment in the past is unnecessary. Therefore, it is possible to provide a comfortable life even during treatment.

In the above explanation, a surgical operation for performing the joining of the bone 51 and the implant component 52 in the body of an animal is explained. However, naturally, it is also possible to remove the bone 51 from the animal and perform the laser machining on the outside of the body of the animal. When the bone 51 is removed from the animal and the bone 51 and the implant component 52 are joined, the bone 51 and the implant component 52 after the joining are returned to the inside of the body of the animal according to necessity. Naturally, the bone after the joining can be returned to the inside of the body of the animal from which the bone is removed or may be returned to the inside of the body of another animal.

It is also possible to easily create an implant component having a new shape in a short time by joining the bone removed from the animal and the implant component in the first embodiment or joining a plurality of the implant components in the first embodiment. In particular, in manufacturing an implant component having a complicated shape in a portion and having a simple shape in the other portion, it is possible to adopt a manufacturing process for separately manufacturing the complicated portion and the simple portion and joining the respective portions in a post-process. Compared with a method of molding the entire implant component through molding by a die or shaving at a time, the manufacturing process is extremely effective for a reduction in a machining time and a reduction in machining costs.

In this way, according to the present invention, in the joining of the bone and the implant component or the joining of the implant components, the bone and the implant component are irradiated with the laser light such as the $CO_2$ laser or the YAG laser. Therefore, it is possible to easily join the bone and the implant component or join the implant components in a short time. The present invention is effective for a surgical operation and manufacturing of a new implant component. In all the embodiments explained above, the safe effect is obtained even if the bone is replaced with a tooth in the explanation about the bone.

INDUSTRIAL APPLICABILITY

As explained above, the implant material according to the present invention is suitable for joining by laser machining and, in particular, suitable for joining of a bone or a tooth and an implant component and joining of implant components.

REFERENCE SIGNS LIST 1 laser machining apparatus
4 laser light
5 foaming portion
6 irradiation position of laser light
10 laser irradiating unit
21 energy-level control unit
22 laser-switching control unit
23 focus-position control unit
30 machining-condition determining unit
41 luminance detecting unit
42 time measuring unit
51 bone
52 implant component
53 weld bead

The invention claimed is:

1. An implant material used for manufacturing of an artificial bone and an artificial tooth root, wherein a quartz glass, or a mixture of a cordierite and the quartz glass is mixed in a hydroxyapatite at least at a weight ratio equal to or higher than 25.7%.

2. The implant material according to claim 1, wherein the weight ratio of the quartz glass, or the mixture of the cordierite and the quartz glass is increased according to predetermined penetration depth of the implant material melted when an implant component to be formed using the implant material is irradiated with laser light.

3. The implant material according to claim 2, wherein, when the weight ratio of the quartz glass, or the mixture of the cordierite and the quartz glass is represented as W (%) and the penetration depth is represented as D (mm), W is set according to D to satisfy a following formula:

$$W \geq 5.8 \times D + 25.7.$$

* * * * *